United States Patent [19]

Buchbinder

[11] Patent Number: 4,960,411
[45] Date of Patent: Oct. 2, 1990

[54] LOW PROFILE STERRABLE SOFT-TIP CATHETER

[75] Inventor: Maurice Buchbinder, San Diego, Calif.

[73] Assignee: Medtronic Versaflex, Inc., San Diego, Calif.

[21] Appl. No.: 213,662

[22] Filed: Jun. 30, 1988

Related U.S. Application Data

[63] Continuation-in-part of Ser. No. 65,122, Jun. 18, 1987, abandoned, which is a continuation of Ser. No. 774,345, Sep. 10, 1985, abandoned, which is a continuation-in-part of Ser. No. 651,806, Sep. 18, 1984, abandoned.

[51] Int. Cl.[5] .................... A61M 29/02; A61M 25/01
[52] U.S. Cl. .......................................... 604/95; 604/96; 128/657
[58] Field of Search .................. 604/95, 280, 264; 128/657, 772

[56] References Cited

U.S. PATENT DOCUMENTS

| | | | |
|---|---|---|---|
| 2,498,692 | 2/1950 | Mains | 604/95 |
| 2,688,329 | 9/1954 | Wallace | 604/95 |
| 4,619,263 | 10/1986 | Frisbie et al. | 604/96 |
| 4,641,654 | 2/1987 | Samson et al. | 604/95 |

Primary Examiner—Stephen C. Pellegrino
Attorney, Agent, or Firm—John L. Rooney

[57] ABSTRACT

This invention relates to steerable catheters. More particularly, this invention relates to a steerable catheter comprising a flexible catheter member having distal and proximal ends and one or more lumens, the single lumen or one of the lumens being closed at its distal end, the one or more other lumens being open, for introduction of a central guide wire or other desired object; a deflection wire having distal and proximal ends and axially extending the length of the catheter member through the lumen having the closed end, the distal end of the deflection wire being embedded in the closed end; and control means attached to the proximal end of the catheter member, the proximal end of the deflection wire extending to the control means and the control means having an engaging means which fixedly engages the deflection wire.

43 Claims, 9 Drawing Sheets

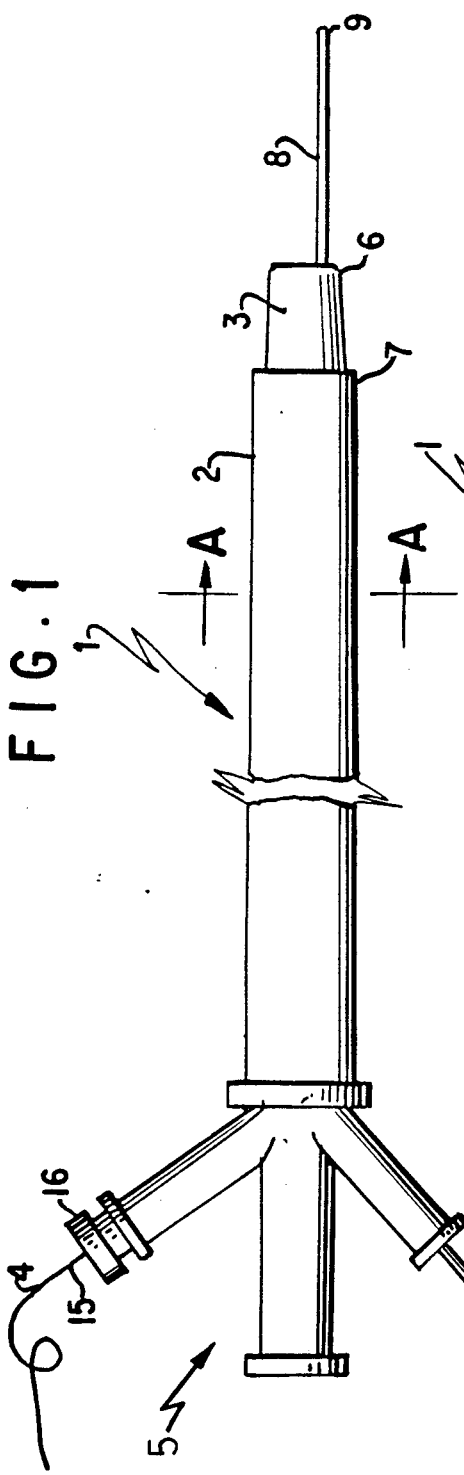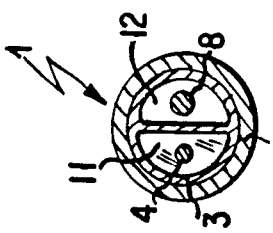

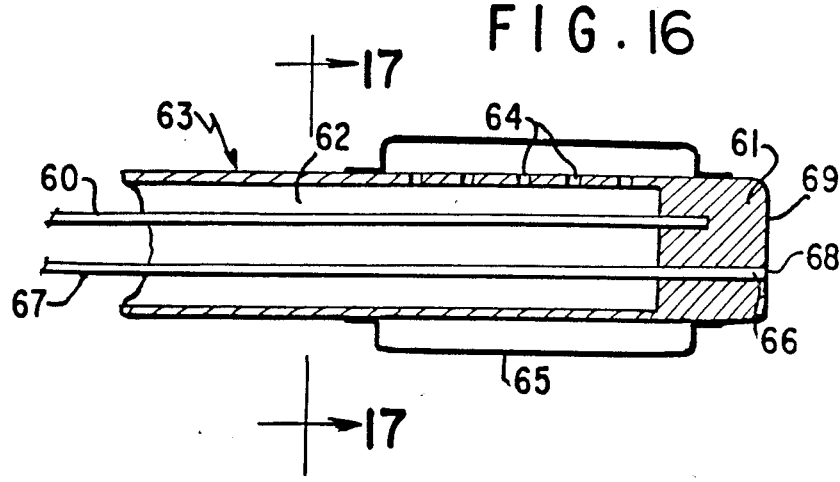
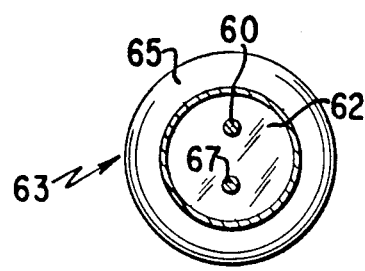
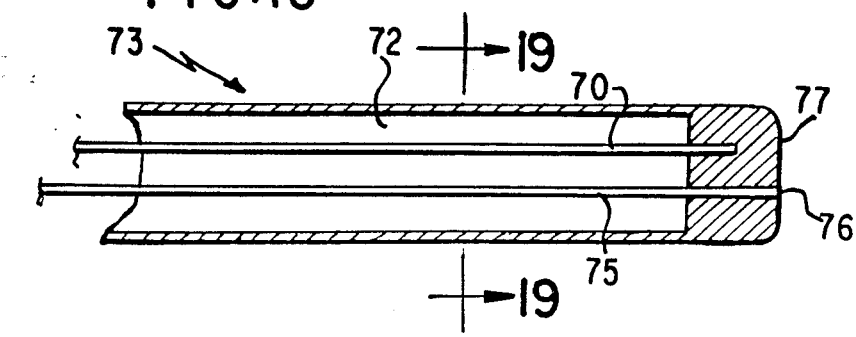
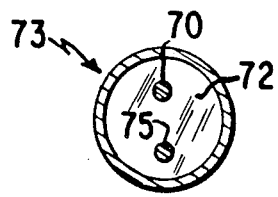

LOW PROFILE STERRABLE SOFT-TIP CATHETER

CROSS-REFERENCE TO RELATED APPLICATIONS

This application is a continuation-in-part application of co-pending U.S. patent application Ser. No. 65,122, filed June 18, 1987 now abandoned; co-pending U.S. Pat. application Ser. No. 193,201, filed May 9, 1988 now abandoned; and co-pending U.S. patent application Ser. No. 48,850, filed May 12, 1987, now abandoned which is a continuation of U.S. Pat. application Ser. No. 774,345, filed Sept. 10, 1985, now abandoned, which is a continuation-in-part of U.S. Pat. application Ser. No. 651,806, filed Sept. 18, 1984, now abandoned, all of which are incorporated herein by reference.

FIELD OF THE INVENTION

This invention relates to steerable catheters. More particularly, this invention relates to steerable soft-tip catheters and a method of using same, especially in the cardiovascular field.

BACKGROUND OF THE INVENTION

Catheters comprise tube-like members that are inserted into the body for various medical reasons, some diagnostic and others therapeutic. While in many instances the steerability or directionality of such catheters is of concern, steerability is particularly important with regard to certain urological or cardiovascular applications.

There have been various attempts to develop steerable catheters. For example, U.S. Pat. No. 1,060,665 describes an early attempt to provide a catheter capable of some direction. However, the device disclosed in this patent, as well as catheters and catheter guides disclosed in later patents, such as U.S. Pat. Nos. 2,574,840 and 2,688,329, tend to be characterized by only limited directionality.

In addition, some supposedly steerable catheters are too large and rigid to be of practical use in cardiovascular techniques. See, for example, U.S. Pat. Nos. 3,470,876 and 3,605,725, where wires equidistantly positioned along the length of a catheter are connected to a steering means which pulls on the wires to cause the distal end of the catheter to go in a desired direction. Moreover, U.S. Pat. Nos. 3,521,620, 3,547,103, 3,625,200, and 4,020,829 describe coil spring guide wires that have a certain degree of directionality but are too rigid for safe usage in certain delicate cardiovascular procedures.

According to U.S. Pat. No. 4,033,331, a coronary catheter has a main lumen and a shaping wire lumen. When the wire is withdrawn through the shaping wire lumen, the catheter assumes certain predetermined configurations. While this so-called steerable catheter is useful in some cardiovascular applications, such as positioning the initial guiding catheter guide through which other devices are guided, its limited directionality and limited tip control preclude extensive use.

A medical procedure known as percutaneous transluminal coronary angioplasty (PTCA) was developed in approximately 1976–1977 by Dr. Andreas Gruntzig. According to this procedure, blockage in a coronary artery can be reduced by positioning a balloon dilatation catheter across the blockage and then inflating the balloon, which causes the blockage to decrease. Such positioning requires that the balloon dilatation catheter be "steered" into place, that is, across the stenotic lesion causing the blockage, by manipulation at the proximal end of the catheter.

The procedure is actually somewhat complex, consisting of introducing a catheter system via the femoral or brachial artery under local anesthesia. A pre-shaped guiding catheter is positioned into the orifice of the coronary artery, and through this guiding catheter a second, dilatation catheter is advanced into the branches of the coronary artery. The dilatation catheter has an elliptically shaped balloon portion near the tip which can be inflated and deflated. After traversal of the stenotic lesion of the coronary artery, the balloon portion is inflated with fluid, which dilates the lumen of the vessel.

The PTCA procedure and equipment have become increasingly refined over the past seven years. The first marketable PTCA apparatus consisted of a small catheter with a single balloon port and no central lumen, that is, a so-called "fixed wire" system, which terminated in lateral openings at the distal end thereof. This system, which is the subject of U.S. Pat. No. 4,195,637, was designed by Dr. Gruntzig and was marketed in the United States by USCI. The fixed wire catheter system disclosed in U.S. Pat. No. 4,195,637 comprises a balloon dilatation catheter and a low friction guide catheter consisting of one tubular member fitted into a more rigid, shrunk-on tubular member that is not co-extensive. The distal end of the balloon dilatation catheter has a flexible tip advantageously fabricated from a spring steel wire.

In 1980–1981, Dr. John Simpson, working at Stanford University, began to modify the fixed wire system and eventually developed a catheter with a free central lumen for movable guide wires and with a dilatation balloon formed from the outer surface covering in a unitary, that is, one-piece, construction. This catheter system is the subject of U.S. Pat. No. 4,323,071, which is assigned to Advanced Cardiovascular Systems, Inc. (ACS), formerly known as Advanced Catheter Systems, Inc. By use of such a movable wire system, one could more readily select the desired coronary artery and get to smaller branches since the movable guide wires are inherently smaller and more flexible than the fixed wire system. Subsequent to the development of the catheter with movable guide wires, known as the Simpson-Robert system and marketed by ACS, USCI has abandoned the fixed wire system and has marketed a similar device, calling it the steerable catheter, DILA ®.

Samson, U.S. Pat. No. 4,516,972 issued May 14, 1985, to ACS. This patent is directed to a guide catheter having a helically wound ribbon of flexible material imbedded in the wall of the catheter to provide torsional rigidity.

There is a further catheter system in use known as the Hartzler low profile catheter system, which is the subject of U.S. Pat. No. 4,582,181. According to this catheter system a balloon dilatation catheter has a concentrically contained guide wire extending the length of said catheter. Moreover, the distal end of the guide wire extends a short distance beyond the distal end of the balloon dilatation catheter and is affixed to the distal end of the balloon dilatation catheter.

The catheter system with movable guide wires and the low profile catheter system each represent an advance but still have disadvantages such as limited steerability, which is at present dependent upon the torquability, or torque control, of the movable wire. Steerability is highly significant in a cardiovascular procedure such as PTCA, or angioplasty, because less steerability results in greater time spent in the body and more possible patient trauma. Multiple insertions of guide wires and catheters can lead to thrombosis in that coagulation may commence along a guide wire surface and be forced into the heart when a catheter is slid over the guide wire. Furthermore, there are some blockages which simply can not be reached with presently known equipment.

There is definitely a need for more steerable catheter means, especially means useful in a procedure such as PTCA. Preferably such catheter means should have the following characteristics:

1. The catheter means may have an outer catheter shaft and an inner catheter to prevent bending of the inner catheter shaft, thus allowing more precise tip control.

2. The entire catheter (outer and inner) must be small enough to compare favorably with already existing small dilatation catheters.

3. The catheter should be capable of rotational and deflective movement. Rotational movement of the steering tip should be precise enough to provide as close to 1:1 torque as possible. This would make the device very useful since it could ultimately be substituted for high torque wires already available.

4. The inner catheter must be free enough to rotate inside the outer catheter so that the tip may turn freely in case another turning axis is needed (superior/inferior vs. lateral).

5. The steering catheter means should optionally have a balloon inflation port, if the catheter's o.d. is small enough to be competitive with the standard dilatation catheters. If this is the case, the space between the inner and outer catheters could be used as an inflation port.

OBJECTS OF THE INVENTION

It is an object of the invention to provide a steerable soft-tip catheter.

It is also an object of the invention to provide a steerable catheter useful in cardiovascular applications.

It is a further object of the invention to provide a delivery means and a method of using said delivery means to deliver objects such as guide wires or balloons to various parts of the cardiac and vascular system as well as the body.

It is a yet further object of the invention to provide a catheter means comprising:

an outer flexible catheter shell having distal and proximal ends, an inner flexible catheter having distal and proximal ends and two or more lumens extending axially therethrough, one of said lumens being closed at its distal end, the one or more other lumens being patent, i.e., open, for introduction of a central guide wire or other desired object, the inner catheter extending axially through the outer catheter shell, and the distal end of the inner catheter protruding distally beyond the distal end of the outer catheter shell, a steering wire having distal and proximal ends and axially extending the length of the inner catheter through the lumen having the closed end, the distal end of the wire being embedded in said closed end, and control means attached to the proximal ends of the outer catheter shell and the inner catheter, the proximal end of the steering wire extending to the control means and the control means having an engaging means which fixedly engages said steering wire to cause the steering wire to longitudinally displace either toward or away from the distal end of the catheter means, said displacement causing the distal end of the inner catheter to bend out of or toward the plane of the longitudinal axis of the inner catheter, the control means having a passageway in fluid connection with at least one open lumen, and the engaging means of the control means fixedly engaging the steering wire so that when the control means is rotated, the catheter and the steering wire both rotate substantially together to cause the distal end of the inner catheter to rotate.

It is additionally an object of the invention to provide a catheter means comprising:

a flexible catheter having distal and proximal ends and one or more lumens, preferably one to three lumens, the single lumen being closed at its distal end or, if there are two or more lumens, at least one of said lumens being closed at its distal end and the remaining lumen or lumens being open, for introduction of a central guide wire or other desired object, a steering wire having distal and proximal ends and extending the length of the catheter through a lumen having a closed end, the distal end of the wire being embedded in said closed end, and control means attached to the proximal end of the catheter, the proximal end of the steering wire extending through the control means and the control means having an engaging means which fixedly engages said steering wire to cause the steering wire to longitudinally displace either toward or away from the distal end of the catheter, said displacement causing the distal end of the catheter to bend out of or toward the plane of the longitudinal axis of the catheter, the control means having a passageway in fluid connection with at least one open lumen and the engaging means of the control means fixedly engaging the steering wire so that when the control means is rotated, the catheter and the steering wire both rotate substantially together to cause the distal end of the catheter to rotate.

These and other objects of the invention will become more apparent in the discussion below.

BRIEF DESCRIPTION OF THE DRAWINGS

FIG. 1 represents a planar view of an embodiment of the invention;

FIG. 2 represents a cross-sectional view along line A—A of the embodiment of the invention shown in FIG. 1;

FIG. 3 represents a partial, longitudinal, cross-sectional view of the distal end of the embodiment of the invention shown in FIG. 1;

FIGS. 8, 10, 12, 14, 16, 18, 20, and 22 each represent a partial, longitudinal, cross-sectional view of a further embodiment of the invention;

FIGS. 9, 11, 13, 15, 17, 19, 21, and 23 each represent a cross-sectional view of the embodiment of the invention represented by FIGS. 8, 10, 12, 14, 16, 18, 20, and 22, respectively.

DETAILED DESCRIPTION OF THE INVENTION

Figure 7:
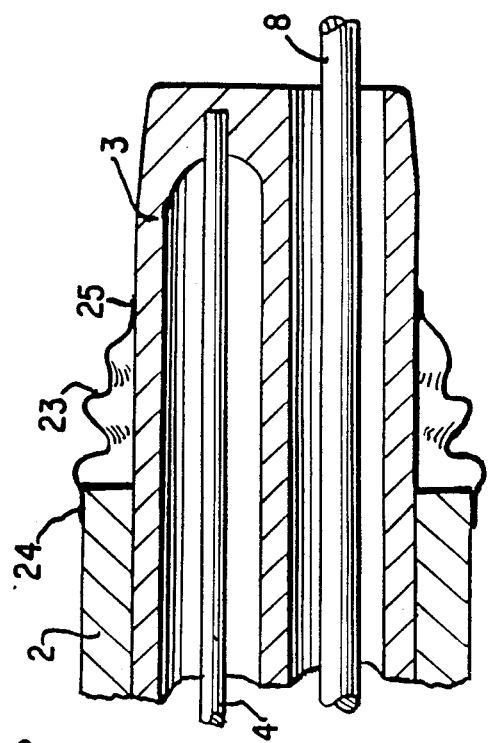
FIG. 7 represents a partial, longitudinal, cross-sectional view of the distal end of another embodiment of the invention.

Applicant has surprisingly developed a soft-tip, flexible and steerable catheter means, or delivery means, which is much more useful than those previously known. According to the invention, a catheter means comprises:

an outer flexible catheter shell having distal and proximal ends, an inner flexible catheter having distal and proximal ends and two or more lumens extending axially therethrough, one of said lumens being closed at its distal end, the one or more other lumens being patent, i.e., open, for introduction of a central guide wire or other desired object, the inner catheter extending axially through the outer catheter shell, and the distal end of the inner catheter protruding distally beyond the distal end of the outer catheter shell, a steering wire having distal and proximal ends and axially extending the length of the inner catheter through the lumen having the closed end, the distal end of the wire being embedded in said closed end, and control means attached to the proximal ends of the outer catheter shell and the inner catheter, the proximal end of the steering wire extending to the control means and the control means having an engaging means which fixedly engages said steering wire to cause the steering wire to longitudinally displace either toward or away from the distal end of the catheter means, said displacement causing the distal end of the inner catheter to bend out of or toward the plane of the longitudinal axis of the inner catheter, the control means having a passageway in fluid connection with at least one open lumen, and the engaging means of the control means fixedly engaging the steering wire so that when the control means is rotated, the catheter and the steering wire both rotate substantially together to cause the distal end of the catheter to rotate.

In another embodiment of the invention, a catheter means comprises:

a flexible catheter having distal and proximal ends and one or more lumens, preferably one to three lumens, the single lumen being closed at its distal end or, if there are two or more lumens, at least one of said lumens being closed at its distal end and the remaining lumen or lumens being open, for introduction of a central guide wire or other desired object, a steering wire having distal and proximal ends and extending the length of the catheter through the lumen having a closed end, the distal end of the wire being embedded in said closed end, and control means attached to the proximal end of the catheter, the proximal end of the steering wire extending through the control means and the control means having an engaging means which fixedly engages said steering wire to cause the steering wire to longitudinally displace either toward or away from the distal end of the catheter, said displacement causing the distal end of the catheter to bend out of or toward the plane of the longitudinal axis of the catheter, the control means having a passageway in fluid connection with at least one lumen that is open and the engaging means of the control means fixedly engaging the steering wire so that when the control means is rotated, the catheter and the steering wire both rotate substantially together to cause the distal end of the catheter to rotate.

The lumens within the catheters may carry various objects and/or may function as other than mere conduits for such objects. For example, a lumen may contain a fixed or movable guide wire, a retractable pressure sensing fiber, a light or laser-conducting means, such as a fiber optic bundle, or an inflatable dilatation balloon. Also, radiopaque fluids or active substances may be transmitted through a lumen, or a lumen may itself be used as a pressure sensor.

The invention can perhaps be better understood by making reference to the drawings. In FIG. 1, catheter means 1 is essentially comprised of outer catheter shaft or shell 2, inner catheter 3, steering wire 4, and control means 5. Catheter shell 2 substantially encloses inner catheter 3, which optionally is freely rotatable within catheter shaft 2.

Distal end 6 of inner catheter 3 projects out of the distal end 7 of catheter shell 2. This projection, that is, the length between distal ends 6 and 7, may vary from about 0.5 to 25 cm, preferably from about 1 to 20 cm, more preferably from about 2 to 10 cm. Distal end 7 may act to define a point or area at which the distal portion of inner catheter will begin to deflect for steerability.

A primary purpose of the invention is to provide a vehicle for delivering certain objects to parts of the body with specific steering control. In the embodiment of the invention shown in FIG. 1, a movably controlled, or movable, guide wire 8 extends the length of catheter means 1, the distal end 9 of movable guide wire 8 projecting out of inner catheter 3 and the proximal end 10 of movable guide wire 8 extending through control means 5.

As can be seen from FIGS. 2 and 3, inner catheter 3 has two lumens, steering lumen 11 and open lumen 12, through which movable guide wire 8 is introduced. The distal end 13 of steering lumen 11 is closed, and the distal end 14 of steering wire 4 is embedded from about 0.1 to 7 cm, preferably from about 1 to 5 cm, into said closed distal end 13.

The proximal end 15 of steering wire 4 extends to or through control means 5 and is fixedly held by torque or engaging means 16. Movement, for example, turning, of engaging means 16 causes wire 4 to shorten or lengthen relative to inner catheter 3, which in turn causes the distal end 6 of inner catheter 3 to bend away from the longitudinal axis of catheter shell 2. In the alternative embodiment steering wire 4 extends through a slidably engaging means, where steering wire 4 is pulled or released, i.e., push-pulled, to cause distal end 6 to bend, and the slidably engaging means is tightened or released to hold distal end 6 in position or to allow steering wire 4 to slide and distal end 6 to move, respectively.

Inner catheter 3 shown in the drawings is depicted with two lumens. However, it is within the scope of the invention that inner catheter 3 could have three or more lumens, dependent upon the particular application.

Figure 4:
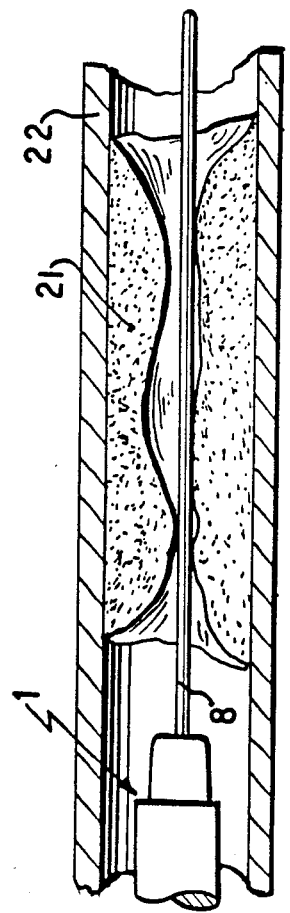
FIG. 4 represents a planar view of the distal end of a coronary dilatation catheter as it extends from the distal end of an embodiment of the invention.

FIG. 4 shows the distal end of an embodiment of the invention with the distal portion of a balloon dilatation catheter 17 projecting beyond the distal end 6 of inner catheter 3. When balloon means 18 is inflated, the balloon means 18 presses against blockage in an artery.

Figure 5:
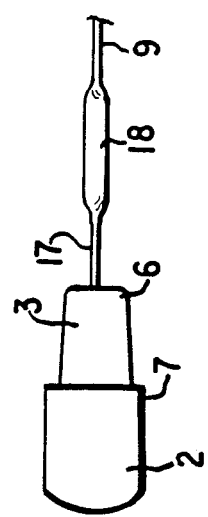
FIG. 5 depicts a patient undergoing the initial stage of a procedure in which an embodiment of the invention would be used.

The delivery system according to the invention can be, as mentioned above, used to introduce or deliver objects to various parts of the body. It is envisioned that said system will be especially useful in cardiovascular applications, such as PTCA. Use of the system in PTCA initially requires the placement of a lead cardiac catheter, such as is shown, for example, in FIG. 5. A cutaneous opening 19 through the skin into the femoral artery in the upper thigh is formed, and then the lead cardiac catheter 20 is positioned essentially as shown. Next, a steerable catheter means according to the invention is threaded into the lead cardiac catheter until the distal end of said catheter means protrudes from the distal end of the lead cardiac catheter. Then, the catheter means according to the invention is steered to the desired position, such as adjacent to a blockage in an artery, at which time a movable guide wire or a balloon dilatation catheter can be maneuvered across the blockage.

Figure 6:
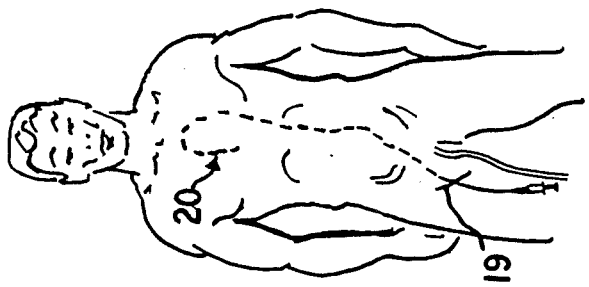
FIG. 6 represents a partially cross-sectional view where an embodiment of the invention is in a position from which a guide wire has been positioned across blockage in an artery.

Such a blockage 21 in an artery 22 is shown in FIG. 6. The movable guide wire 8 has been manipulated across the blockage 21 so that distal end 9 of movable guide 8 extends past blockage 21. Once guide wire 8 is in proper position, a balloon dilatation catheter is then threaded along movable guide wire 8 until it is also in position across blockage 21.

Another embodiment of the invention is represented by FIG. 7, where a dilatation balloon means 23 is attached to catheter shell 2 at point 24 and to inner catheter 3 at point 25. The dilatation balloon means 23 is inflated by a non-compressible fluid, preferably a physiological salt solution and/or an iodinated x-ray contrast medium, that is furnished through the space between catheter shell 2 and inner catheter 3, that is, said space acts as a balloon inflation port. The approximate longitudinal distance between points 24 and 25 is from about 2 to 20 cm, preferably from about 3 to 10 cm.

Figure 8:
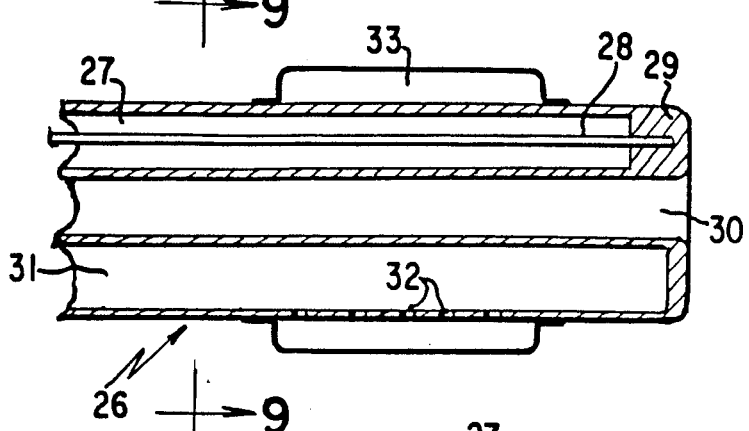
Figure 9:
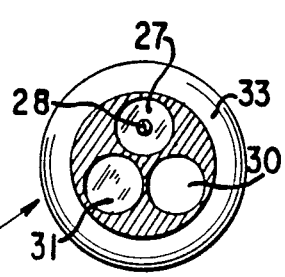

Further embodiments of the invention are set forth in FIGS. 8 to 23. The embodiment represented by FIGS. 8 and 9 comprises a triple lumen catheter 26 wherein steering lumen 27 has a steering wire 28 embedded in the distal end 29 of steering lumen 27. Open lumen 30 provides a passageway for, for example, a movable wire or a retractable pressure sensing fiber (not shown). Balloon dilatation lumen 31 has openings 32 near its distal end to permit inflation of dilatation balloon 33.

Figure 10:
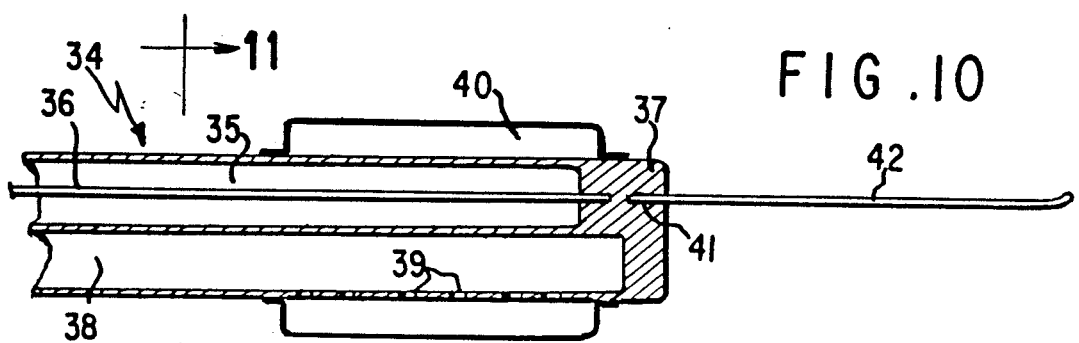
Figure 11:
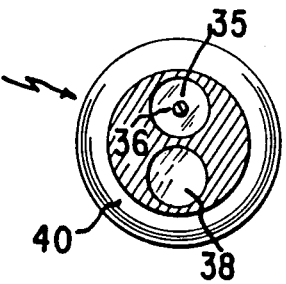

FIGS. 10 to 13 depict double lumen catheter means according to the invention. In FIG. 10, the catheter 34 comprises steering lumen 35 having a steering wire 36 embedded in the distal end 37 of steering lumen 35. Balloon inflation lumen 38 has openings 39 near its distal end to permit inflation of dilatation balloon 40. Also embedded in distal end 37 is the proximal end 41 of a floppy wire flexible tip, or "antenna", 42, which acts primarily to protect the inner surfaces as the catheter is maneuvered through various body passageways and/or to detect small passages in the hollow space or cavity to be dilated. Advantageously the antenna is fabricated from a spring steel wire and is from about 0.5 to 5 cm, preferably from about 1 to 3 cm, in length.

Figure 12:
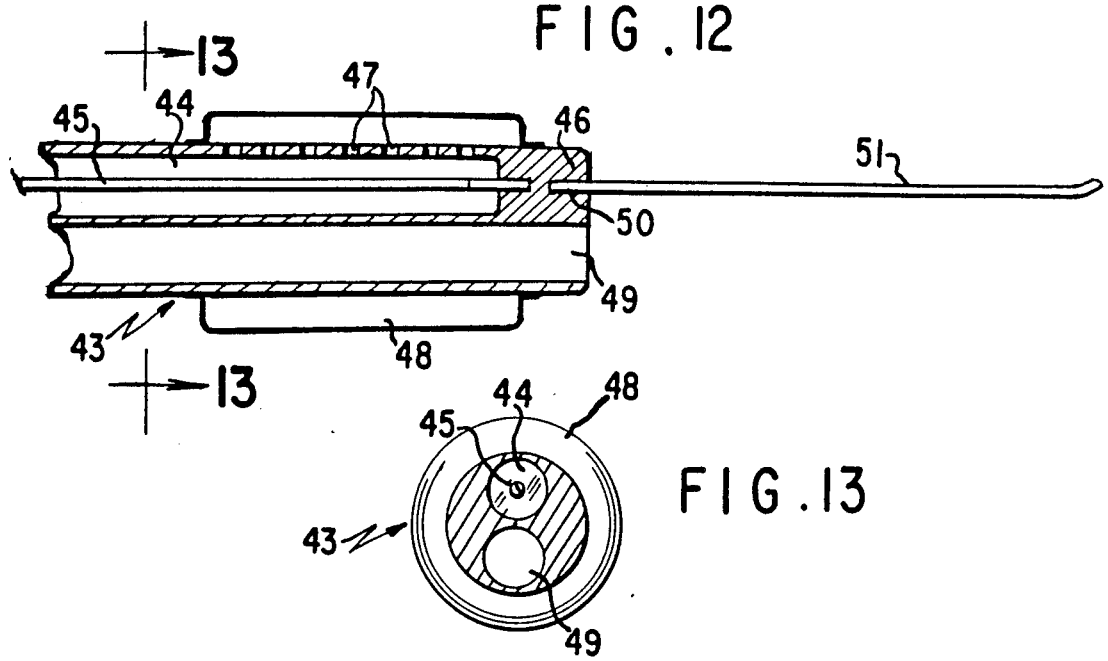
Figure 13:
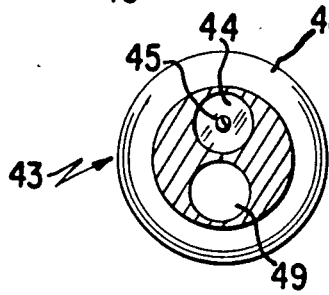
Figure 14:
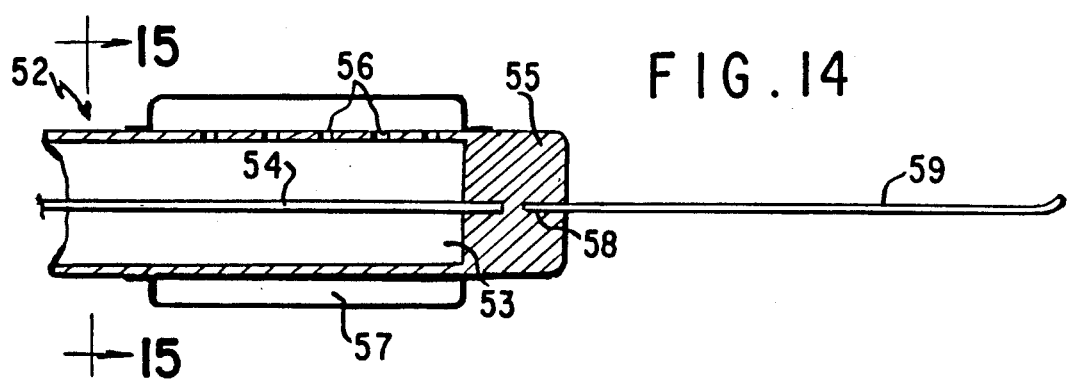
Figure 15:
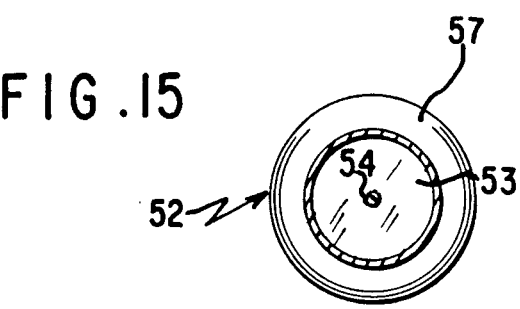
Figure 20:
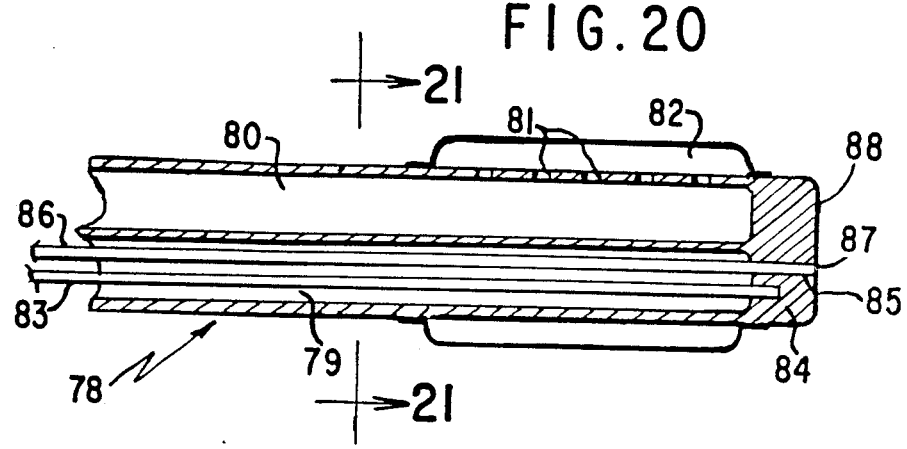
Figure 21:
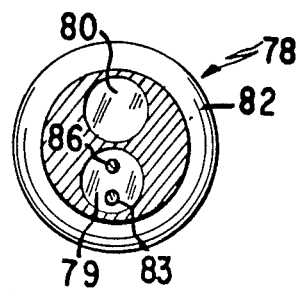

Double lumen catheter 43 represented in FIGS. 12 and 13 has a steering lumen 44 having a steering wire 45 embedded in its distal end 46, said lumen 44 also having openings 47 near distal end 46 to permit inflation of dilatation balloon 48. Open lumen 49 provides a conduit for an object such as a retractable pressure sensing fiber (not shown). The proximal end 50 of an antenna 51 is affixed to the distal end of catheter 43.

The embodiments of the invention shown in FIGS. 14 to 19 are single lumen catheter means. The catheter 52 in FIGS. 14 and 15 comprises a closed lumen 53 having a steering wire 54 embedded in the distal end 55 of closed lumen 53. Closed lumen 53 has openings 56 near distal end 55 to permit inflation of dilatation balloon 57. The proximal end 58 of antenna 59 is also embedded in distal end 55.

According to FIGS. 16 and 17, steering wire 60 is embedded in or near the distal end 61 of closed lumen 62 of catheter 63. Lumen 62 has openings 64 near distal end 61 to permit inflation of dilatation balloon 65. Also, the distal end 66 of a pressure sensing fiber 67 is embedded in distal end 61, the outer surface 68 of pressure sensing fiber distal end 66 comprising a pressure sensing membrane substantially flush with the outer surface 69 of lumen distal end 61. The pressure sensing fiber 67 is a very small fiber which transduces the pressure sensed at distal end 66. Fiber 67 is advantageously from about 1 to 10 microns, preferably from about 5 to 8 microns, in diameter.

The embodiment of the invention set forth in FIGS. 18 and 19 is similar to the embodiment set forth in FIGS. 16 and 17. Steering wire 70 is embedded in the distal end 71 of lumen 72 of catheter 73. The distal end 74 of a pressure sensing fiber 75 is embedded in distal end 71, the outer surface 76 of pressure sensing fiber distal end 74 comprising a pressure sensing membrane substantially flush with the outer surface 77 of lumen distal end 71.

FIGS. 20 to 23 represent double lumen embodiments having a pressure sensing fiber and a steering wire. According to FIGS. 20 and 21, catheter 78 comprises steering lumen 79 and balloon inflation lumen 80, which has openings 81 near its distal end to permit inflation of dilatation balloon 82. Steering lumen 79 has a steering wire 83 embedded in the distal end 84 of steering lumen 79. The distal end 85 of a pressure sensing fiber 86 is also embedded in distal end 84, the outer surface 87 of pressure sensing fiber distal end 85 comprising a pressure sensing membrane substantially flush with the outer surface 88 of the distal end of catheter 78.

Figure 22:
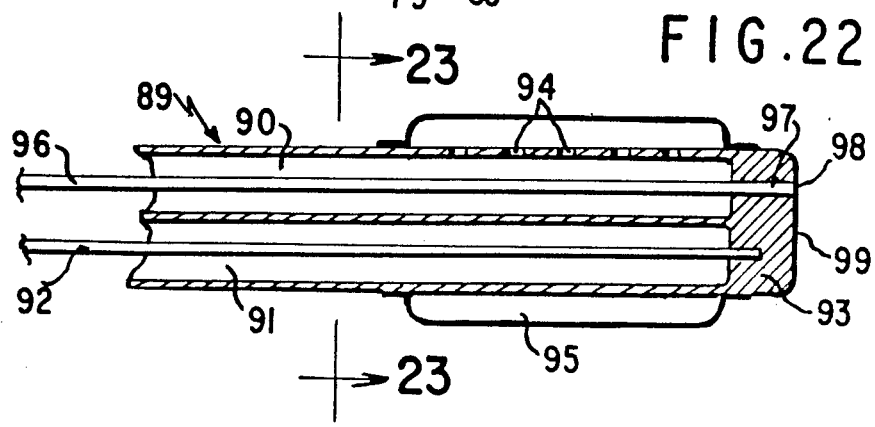
Figure 23:
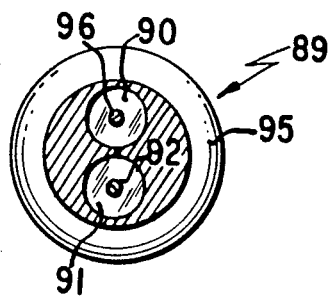

In FIGS. 22 and 23, catheter 89 comprises balloon inflation lumen 90 and steering lumen 91, wherein steering wire 92 is embedded in the distal end 93 of steering lumen 91. Balloon inflation lumen 90 has (1) openings 94 to permit inflation of dilatation balloon 95 and (2) a pressure sensing fiber 96. The distal end 97 of pressure sensing fiber 96 is embedded in the distal end of balloon inflation lumen 90 in a manner such that the outer surface 98 of pressure sensing fiber distal end 97, which comprises a pressure sensing membrane, is substantially flush with the outer surface 99 of the distal end of catheter 89.

In the embodiments of the invention described in FIGS. 8 to 23, the distal ends of the respective catheter means are maneuvered across a blockage in an artery. More particularly, the dilatation balloon means are positioned so that they can be inflated to cause the blockage to decrease. Also, the pressure sensing fibers can make desired pressure readings.

Figure 24:
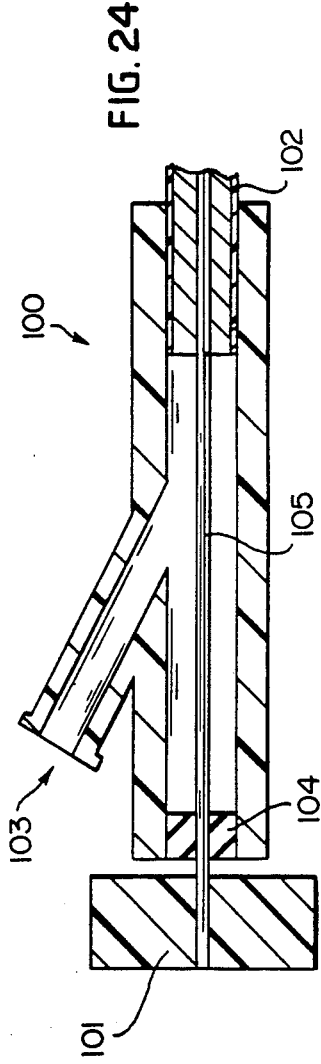
FIGS. 24 to 27 each represent a partially cross-sectional view of a proximal end of one embodiment of the invention.

Each of the embodiments of the invention set forth in FIGS. 1 and 12 to 23 is attached to a suitable control means, having torque control, such as one of those shown in FIGS. 1 and 24 to 27. It is important to note that according to the invention the control means has both push-pull and rotational motion/capability to properly direct the catheter. More particularly, a control means, designated generally as 100, to steer the catheter is shown in FIG. 24. Pushing or pulling deflection knob 101 causes deflection wire 105 to move distally or proximally to cause the distal end (not shown) of a catheter member 102 to deflect out of plane, that is, toward or away from the longitudinal axis or line of catheter member 102. Rotation of the deflection knob 101 together with the entire control means 100 results in rotation of the distal end of catheter member 102 to a desired orientation. An opening or port 103 in the control means 100 and a seal 104 allow fluid to be directed toward the distal end of catheter member 102, for example, for inflation of a dilatation balloon member (not shown).

Figure 25:
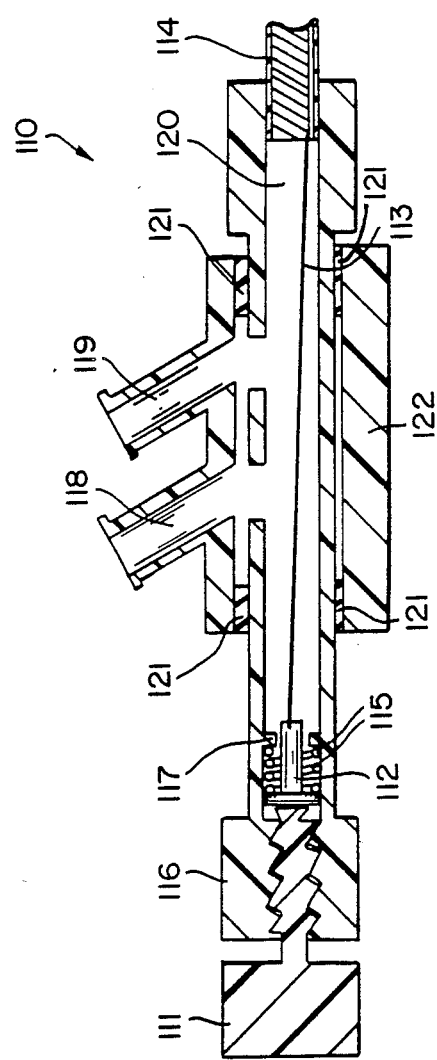
Figure 26:
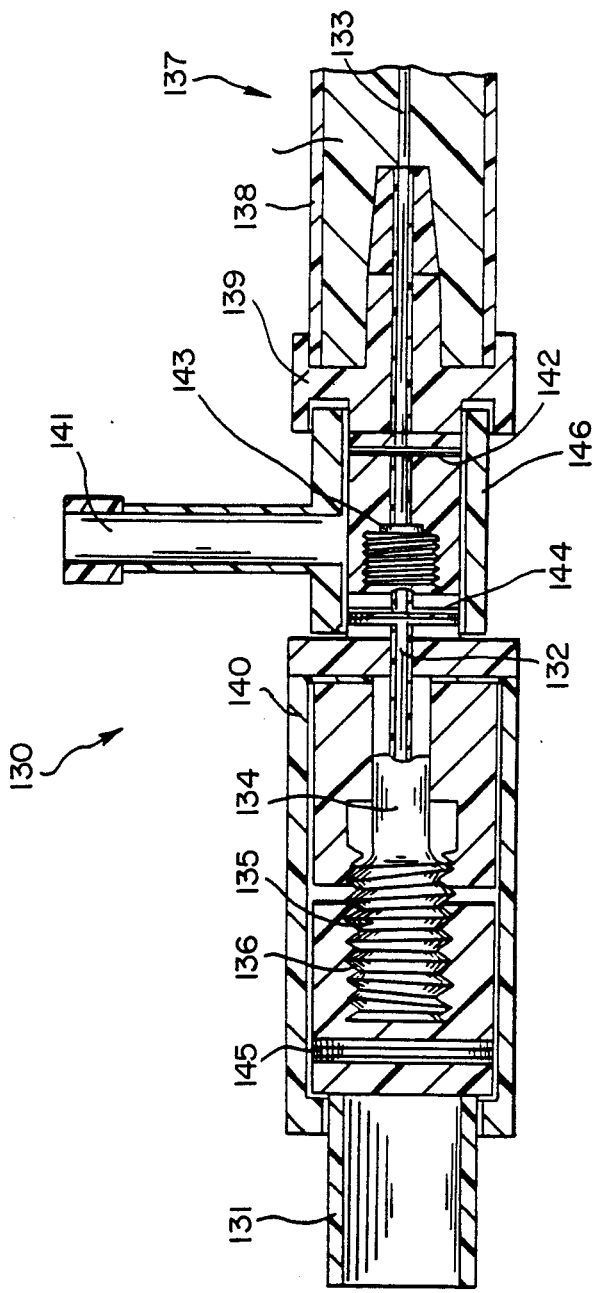
Figure 27:
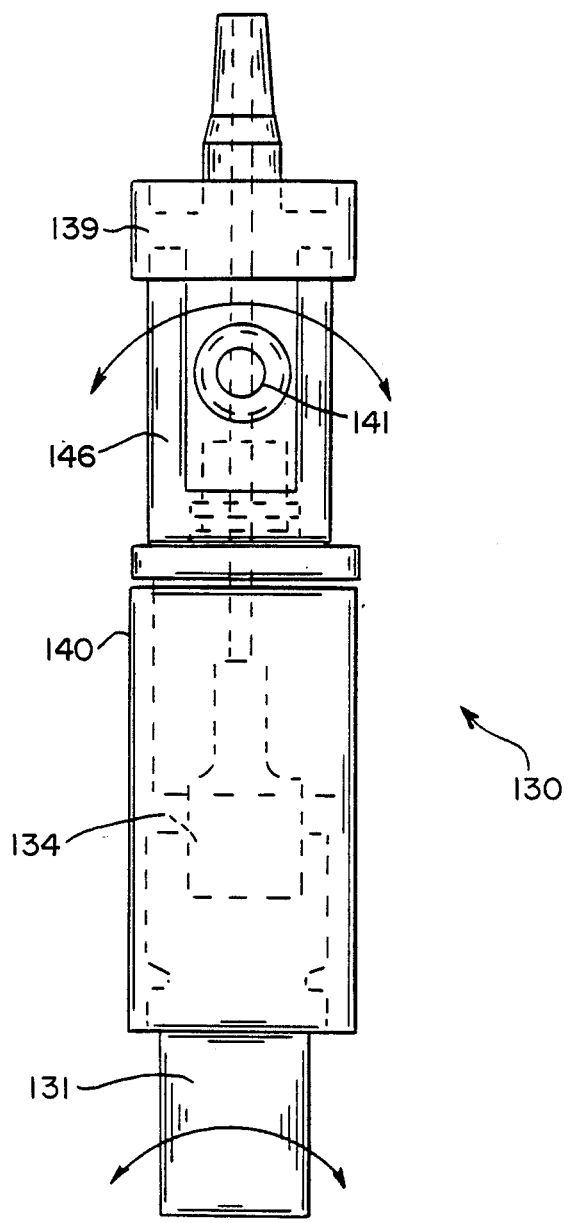

Alternate control means, generally designated as 110 and 130, are shown in FIGS. 25 to 27. Control means 110 employs a threaded or deflection knob 111 for precise tip deflection. Clockwise rotation of the deflection knob 111 causes pressure to be exerted on deflection wire termination block 112, which in turn causes pressure to be exerted distally along the longitudinal axis of deflection wire 113, which in turn causes the distal end (not shown) of catheter member 114 to deflect. When deflection knob 111 is backed out, i.e., rotated in counter-clockwise fashion, a return spring 115 pushes the deflection wire termination block 112 back to its original position and thus allows the catheter member tip (not shown) to straighten. To rotate the catheter, rotation control knob 116 is rotated, which causes catheter member 114 and deflection wire 113 to rotate together.

The termination block 112 has a non-circular, e.g., rectangular or square, cross-section, and any rotational movement of the termination block is limited or prevented by substantially annular sealing/guide means 117. Preferably the only movement by the termination block 112 is in the longitudinal direction, i.e., proximally or distally.

Control means 110 also has ports 118 and 119 that are in fluid communication with a passageway 120, which may in turn be in fluid communication with a lumen (not specifically shown) in catheter member 114, for passage of liquids or other devices, e.g., other catheters, guide wires, pressure monitoring means, optical fibers, and the like, through said lumen. Annular seals 121, preferably made of suitable polymeric material such as TEFLON, allow the port section 122 to remain stationary while the rotation control knob 116 is manipulated.

As shown in FIGS. 26 and 27, control means 130 employs a threaded control or deflection knob 131 for precise tip deflection. The proximal end 132 of the deflection wire 133 is fixedly engaged at engaging member 134, the outer surface of which has threading 135 which engages cooperating threading 136 on the inner surface of the distal portion of deflection knob 131. Rotation of deflection knob 131 causes movement of engaging member 134, which in turn causes movement of the deflection wire 133 along its longitudinal axis, which in turn causes the distal end (not shown) of catheter member 137 to deflect. The proximal end 138 of catheter member 137 is engagingly attached to attachment member 139, which is in turn connected to rotation control member 140. When rotation control member 140 is rotated, catheter member 137 and deflection wire 133 rotate together, which in turn results in rotation of the distal end (not shown) of catheter member 137.

Port 141 is in fluid communication with a lumen (not shown) of catheter member 137, for example, for inflation of a dilatation balloon (not shown). Annular seals 142, 143, 144, and 145 permit the port section 146 to remain stationary while deflection knob 131 and/or rotation control member 140 is manipulated.

In a variation of the control means shown in FIGS. 26 and 27, not shown, a control means comprises a deflection knob having an inflation port in fluid communication with a lumen in the catheter. This arrangement is advantageous in that fewer seals are required and that the external source connecting to the inflation port is less in the way.

Reference has been made to openings 32, 39, 47, 56, 64, 81, and 94, which permit inflation of dilatation balloon means. Said openings should be of sufficient size and in sufficient number to permit quick inflation but not to weaken the catheter means structurally. For example, said openings could comprise from 2 to 12 substantially circular or rectangular openings each having a cross-sectional area of from about 0.01 to 25 mm$^2$, preferably from about 0.05 to 15 mm$^2$.

The inflation and deflation of dilatation balloon means are well-known techniques, and various equipment therefor has been developed. See, for example, U.S. Pat. Nos. 4,231,715, 4,332,254, and 4,439,185 and U.S. Design Pat. No. 274,470.

The particular dimensions of the various aspects of the steerable means according to the invention would be readily apparent to those skilled in the art. The outer catheter shell should be from about 90 to 150 cm, preferably from about 100 to 150 cm, more preferably from about 125 to 145 cm, in length, and the movable inner catheter should be about 1 to 20 cm longer, preferably from about 2 to 10 cm longer. For example, the outer catheter and inner catheter could be about 135 cm to 140 cm in length, respectively. Where there is only a single catheter, said catheter is from about 90 to 170 cm, preferably from about 125 to 165 cm, in length. Guide wires can be from about 150 to 400 cm, preferably about 225 to 325 cm, in length. The steering wire will be substantially coextensive with the inner catheter or a single catheter. Moreover, the steering wire may be tapered in the distal direction, starting at a point from about 1 to 10 cm, preferably from about 2 to 8 cm, proximal of the distal end of the steering wire. Such tapering may be, for example, substantially linear tapering from a diameter of from about 0.020 inches to a diameter of from about 0.005 inches.

The respective diameters of the catheters and lumens will vary according to application. The o.d. of the outer catheter or a single catheter could be from about 0.010 to 0.50 inches, preferably from about 0.030 to 0.30 inches, with or without balloon ports. The inner diameters of each of the lumens in the inner catheter or a single catheter could each be from about 0.0003 to 0.30 inches, preferably from about 0.005 to 0.200 inches, more preferably from about 0.010 to 0.100 inches, and most preferably from about 0.018 to 0.050 inches. Also, there may be a space of from about 0.001 to 0.10 inches, preferably from about 0.005 to 0.025 inches, between the outer surface of the inner catheter and the inner surface of the outer catheter, which space could be used for inflation.

The catheter means of this invention may be formed from any suitable plastic material having a low coefficient of friction, such as plasticized vinyl resins, a polyolefin such as polyethylene, polyvinylchloride, polyamide, synthetic and natural rubbers, and polyurethane elastomers. In most instances the catheter means will have one or more substances or elements to make it radiopaque, so that it can be readily seen by a fluoroscope during medical and/or surgical procedures. Various marking elements which are impervious or only slightly pervious to radiation, such as gold foil, are known for this purpose. The various guide wires useful according to the invention may be any suitable surgical metal or other material which is medically non-reactive.

Although the discussion above relates to use of a balloon dilatation catheter, the invention is not limited to this concept. The catheter means of the invention is essentially a delivery system capable of delivering various objects to desired parts of the body, and the delivery of fluids such as radiopaque fluids, pharmaceuticals, or of other medical devices such as, for example, optical fibers such as quartz fibers useful in delivering laser energy, is within the scope of the invention.

The above-mentioned United States patents are all incorporated herein by reference. In particular, U.S. Pat. Nos. 3,941,119, 4,020,829, 4,033,331, 4,195,637, and 4,323,071 are incorporated herein with respect to methods of using catheters and the discussions of associated equipment.

The preceding specific embodiments are illustrative of the practice of the invention. It is to be understood, however, that other expedients known to those skilled in the art or disclosed herein, may be employed without departing from the spirit of the invention or the scope of the appended claims.

| COMPONENT LIST | |
|---|---|
| No. | Component |
| 1 | catheter means |
| 2 | catheter shell |
| 3 | inner catheter |
| 4 | steering wire |
| 5 | control means |
| 6 | distal end of inner catheter |
| 7 | distal end of catheter shell |
| 8 | guide wire |
| 9 | distal end of guide wire |
| 10 | proximal end of guide wire |
| 11 | steering lumen |
| 12 | open lumen |
| 13 | distal end of steering lumen |
| 14 | distal end of steering wire |
| 15 | proximal end of steering wire |
| 16 | torque means |
| 17 | balloon dilatation catheter |
| 18 | balloon means |
| 19 | cutaneous opening |
| 20 | cardiac catheter |
| 21 | blockage |
| 22 | artery |
| 23 | balloon means |
| 24,25 | attachment point |
| 26 | triple lumen catheter means |
| 27 | steering lumen |
| 28 | steering wire |
| 29 | steering lumen distal end |
| 30 | open lumen |
| 31 | balloon dilatation lumen |
| 32 | openings |
| 33 | dilatation balloon |
| 34 | catheter |
| 35 | steering lumen |
| 36 | steering wire |
| 37 | steering lumen distal end |
| 39 | openings |
| 40 | dilatation balloon |
| 41 | antenna proximal end |
| 42 | antenna |
| 43 | catheter |
| 44 | steering lumen |
| 45 | steering wire |
| 46 | steering lumen distal end |
| 47 | openings |
| 48 | dilatation balloon |
| 49 | open lumen |
| 50 | antenna proximal end |
| 51 | antenna |
| 52 | catheter |
| 53 | closed lumen |
| 54 | steering wire |
| 55 | closed lumen distal end |
| 56 | openings |
| 57 | dilatation balloon |
| 58 | antenna proximal end |
| 59 | antenna |
| 60 | steering wire |
| 61 | closed lumen distal end |
| 62 | closed lumen |
| 63 | catheter |
| 64 | openings |
| 65 | dilatation balloon |
| 66 | pressure sensing fiber distal end |
| 67 | pressure sensing fiber |
| 68 | fiber outer surface |
| 69 | lumen distal end outer surface |
| 70 | steering wire |
| 71 | lumen distal end |
| 72 | lumen |
| 73 | catheter |
| 74 | pressure sensing fiber distal end |
| 75 | pressure sensing fiber |
| 76 | fiber outer surface |
| 77 | lumen distal end outer surface |
| 78 | catheter |
| 79 | steering lumen |
| 80 | balloon inflation lumen |
| 81 | openings |
| 82 | dilatation balloon |
| 83 | steering wire |
| 84 | steering lumen distal end |
| 85 | pressure steering fiber distal end |
| 86 | pressure sensing fiber |
| 87 | fiber outer surface |
| 88 | catheter distal end outer surface |
| 89 | catheter |
| 90 | balloon inflation lumen |
| 91 | steering lumen |
| 92 | steering wire |
| 93 | steering lumen distal end |
| 94 | openings |
| 95 | dilatation balloon |
| 96 | pressure sensing fiber |
| 97 | pressure sensing fiber distal end |

-continued

COMPONENT LIST

| No. | Component |
|---|---|
| 98 | fiber distal end outer surface |
| 99 | catheter distal end outer surface |
| 100 | control means |
| 101 | deflection knob |
| 102 | catheter member |
| 103 | port |
| 104 | seal |
| 105 | deflection wire |
| 110 | control means |
| 111 | deflection knob |
| 112 | termination block |
| 113 | deflection wire |
| 114 | catheter member |
| 115 | return spring |
| 116 | rotation control knob |
| 117 | annular sealing/guide means |
| 118, 119 | port |
| 120 | passageway |
| 121 | annular seal |
| 122 | port section |
| 130 | control means |
| 131 | deflection knob |
| 132 | proximal end of deflection wire |
| 133 | deflection wire |
| 134 | engaging member |
| 135, 136 | threading |
| 137 | catheter member |
| 138 | proximal end of catheter member |
| 139 | attachment member |
| 140 | rotation control member |
| 141 | port |
| 142, 143, 144, 145 | annular seal |
| 146 | port section |

I claim:

1. A steerable catheter means comprising:
an outer catheter shaft,
a flexible catheter member located within said outer catheter shaft having distal and proximal ends and one or more lumens extending therethrough, at least one of said lumens being closed at its distal end, the other lumen or lumens being open at the distal end or ends thereof,
a deflection were having distal and proximal ends and axially extending through a lumen having a closed end, the distal end of said deflection wire being embedded in said closed end, and
control means attached to the proximal end of said catheter member, the proximal end of said deflection wire extending through said control means and said control means having an engaging means which fixedly engages said deflection wire, rotation of said engaging means causing said deflection wire to longitudinally displace either toward or away from the distal end thereof, said displacement causing the distal end of said catheter member to bend out of or toward the line of he longitudinal axis of said catheter member, and the engaging means of said control means fixedly engaging said deflection wire so that when said control means is rotated, said catheter member and said deflection wire both rotate together to cause the distal end of said catheter member to rotate about its longitudinal axis.

2. A steerable catheter means consisting essentially of:
an outer catheter shaft,
a flexible catheter member located within said outer catheter shaft having distal and proximal ends and one or more lumens extending therethrough, at least one of said lumens being closed at its distal end, the other lumen or lumens being open at the distal end or ends thereof,
a deflection wire having distal and proximal ends and axially extending through a lumen having a closed end, the distal end of said deflection wire being embedded in said closed end, and
control means attached to the proximal end of said catheter member, the proximal end of said defection wire extending to said control means, said control means having engaging means which fixedly engages the proximal end of said deflection wire to cause said deflection wire to be displaced distally or proximally, said displacement causing the distal end of said catheter member to bend out of or toward the line of the longitudinal axis of said catheter member, and said control means having rotation means to cause said deflection wire and said catheter member to rotate together to cause the distal end of said catheter member to rotate about its longitudinal axis.

3. The steerable catheter means of claim 2, wherein said catheter comprises from 1 to 3 lumens.

4. The steerable catheter means of claim 2, wherein said catheter member has at least two lumens and one of said lumens is open.

5. The steerable catheter means of claim 4, wherein the open lumen is capable of having a balloon dilatation catheter or a retractable pressure sensor threaded therethrough.

6. The steerable catheter means of claim 2, wherein the outer surface of said catheter member near the distal portion thereof comprises dilatation balloon means.

7. The steerable catheter means of claim 6, wherein a closed lumen has openings near its distal end and said openings are arranged to permit inflation of said dilatation balloon means.

8. The steerable catheter means of claim 2, wherein a closed lumen has a pressure sensing fiber therein, said pressure sensing fiber having distal and proximal ends, the distal end of said pressure sensing fiber comprising a pressure sensing membrane, and the distal end of said pressure sensing fiber extending through the distal end of said catheter member whereby the pressure sensing membrane is substantially flush with the outer surface of the distal end of said catheter member.

9. The steerable catheter means of claim 2, wherein a flexible tip has proximal and distal ends and the proximal end thereof is affixed or embedded in the distal end of the catheter member.

10. The steerable catheter means of claim 9, wherein the flexible tip is a floppy wire comprised of spring steel wire.

11. The steerable catheter means of claim 2, wherein said catheter member comprises a lumen open at its distal end and the proximal end of said lumen is in fluid communication with a passageway in said control means.

12. A steerable catheter means consisting essentially of:
an outer catheter shaft,
a flexible catheter located within said outer catheter shaft having distal and proximal ends and two lumens extending therethrough, one of said lumens being closed at its distal end, and the other lumen being open at its distal end, a deflection wire having distal and proximal ends and axially extending through the lumen having the closed end, the distal end of said deflection wire being embedded in said closed end, and control means attached to the proximal end of said catheter means, the proximal end of said deflection wire extending to said control means, said control means having engaging means which fixedly engages the proximal end of said deflection wire to cause said deflection wire to be displaced distally or proximally, said displacement causing the distal end of said catheter member to bend out of or toward the line of the longitudinal axis of said catheter member, and said control means having rotation means to cause said deflection wire and said catheter member to rotate together to cause the distal end of said catheter member to rotate about its longitudinal axis.

13. A steerable catheter means consisting essentially of:

an outer catheter shaft, a flexible catheter movably located within said outer catheter shaft having distal and proximal ends and one or more lumens extending therethrough, each of said lumens being closed at its distal end, a deflection wire having distal and proximal end s and axially extending through the lumen having a closed end, the distal end of the deflection wire being embedded in said closed end, and control means attached to the proximal end of said catheter member, the proximal end of said deflection wire extending to said control means, said control means having engaging means which fixedly engages the proximal end of said deflection wire to cause said deflection wire to be displaced distally or proximally, said displacement causing the distal end of said catheter member to bend out of or toward the line of the longitudinal axis of said catheter member, and said control means having rotation means to cause said deflection wire and said catheter member to rotate together to cause the distal end of said catheter member to rotate about its longitudinal axis.

14. A steerable catheter means comprising:

an outer flexible catheter member having distal and proximal ends, an inner flexible catheter member having distal and proximal ends and two or more lumens extending therethrough, one of said lumens being closed at its distal end, the one or more other lumens being open distally, the inner catheter member extending through the outer catheter member, and the distal end of the inner catheter member protruding distally beyond the distal end of the outer catheter member, a deflection wire having distal and proximal ends and extending the length of the inner catheter member through the lumen having the closed end, the distal end of the wire being embedded in said closed end, and control means attached to the proximal end of the inner catheter member, the proximal end of the deflection wire extending to the control means, the control means having engaging means which fixedly engages the proximal end of said deflection wire to cause said deflection wire to be displaced distally or proximally, said displacement causing the distal end of the inner catheter member to bend out of or toward the line of its longitudinal axis, the control means having a passageway in fluid connection with at least one open lumen, and the control means having rotation means to cause said deflection wire and the inner catheter member to rotate together to cause the distal end of the inner catheter member to rotate about its longitudinal axis.

15. The catheter means of claim 14 which also comprises a guide wire extending through an open lumen, the guide wire having distal and proximal ends, the distal end of the guide wire protruding distally beyond the distal end of the inner catheter member, and the proximal end of the guide wire extending through the passageway in the control means.

16. The catheter means of claim 14 which also comprises a balloon dilatation catheter extending through an open lumen, the balloon dilatation catheter having distal and proximal ends, the distal end of the balloon dilatation catheter having inflatable dilatation balloon means adjacent said distal end and protruding distally beyond the distal end of the inner catheter member, and the proximal end of the balloon dilatation catheter extending through the passageway in the control means.

17. The catheter means of claim 16, wherein the balloon dilatation catheter has a guiding lumen therein and a guide wire having proximal and distal ends extends the length of the guiding lumen, the distal end of the balloon dilatation catheter protruding distally beyond the distal end of the inner catheter member, and the distal end of the guide wire extending distally beyond the distal end of the balloon dilatation catheter.

18. The catheter means of claim 14, wherein the inner catheter member has two lumens.

19. The catheter means of claim 14 which comprises balloon dilatation means arranged on the outer surface of the inner catheter member adjacent its distal end.

20. The catheter means of claim 14, wherein the inner catheter member is freely movable within the outer catheter shell.

21. The catheter means of claim 14, wherein the deflection wire is tapered at its distal end.

22. A steerable catheter means comprising:

an outer flexible catheter member having distal and proximal ends, an inner flexible catheter member having distal and proximal ends and two or more lumens extending therethrough, one of said lumens being closed at its distal end, the one or more other lumens being open distally, the inner catheter member extending through the outer catheter member, and the distal end of the inner catheter member protruding distally beyond the distal end of the outer catheter member, a deflection wire having distal and proximal ends and extending the length of the inner catheter member through the lumen having said closed end, the distal end of the wire being embedded in said closed end, and control means attached to the proximal ends of the outer catheter member and the inner catheter member, the proximal end of the deflection wire extending to the control means, the control means having engaging means which fixedly engages the proximal end of said deflection wire to cause said deflection wire to be displaced distally or proximally, said displacement causing the distal end of the inner catheter member to bend out of or toward the line of its longitudinal axis, the control means having a passageway in fluid communication with at least one open lumen, and the control means having rotation means to cause said deflection wire and the inner catheter member to rotate substantially together to cause the distal end of the inner catheter member to rotate about its longitudinal axis.

23. The catheter means of claim 22 which also comprises a guide wire extending through an open lumen, the guide wire having distal and proximal ends, the distal end of the guide wire protruding distally beyond the distal end of the inner catheter member, and the proximal end of the guide wire extending through the passageway in the control means.

24. The catheter means of claim 22 which also comprises a balloon dilatation catheter extending through an open lumen, the balloon dilatation catheter having distal and proximal ends, the distal end of the balloon dilatation catheter having inflatable dilatation balloon means adjacent said distal end and protruding distally beyond the distal end of the inner catheter member, and the proximal end of the balloon dilatation catheter extending through the passageway in the control means.

25. The catheter means of claim 24, wherein the balloon dilatation catheter has a guiding lumen therein and a guide wire having proximal and distal ends extends the length of the guiding lumen, the distal end of the balloon dilatation catheter protruding distally beyond the distal end of the inner catheter member, and the distal end of the guide wire extending distally beyond the distal end of the balloon dilatation catheter.

26. The catheter means of claim 22, wherein the inner catheter member has two lumens.

27. The catheter means of claim 22 which comprises balloon dilatation means arranged on the outer surfaces of the outer catheter member and the inner catheter member adjacent the distal end thereof.

28. The catheter means of claim 22 which comprises balloon dilatation means arranged on the outer surface of the distal end of the inner catheter member adjacent its distal end.

29. The catheter means of claim 22, wherein the deflection wire is tapered at its distal end.

30. A steerable catheter means comprising:
an outer flexible catheter member having distal and proximal ends,
an inner flexible catheter member having distal and proximal ends and two or more lumens extending therethrough, one of said lumens being closed at its distal end, the other lumen or lumens being open at the distal end or ends thereof, the inner catheter member extending through the outer catheter member, and the distal end of the inner catheter member protruding distally beyond the distal end of the outer catheter member,
a deflection wire having distal and proximal ends and extending the length of the inner catheter member through the lumen having the closed end, the distal end of the deflection wire being embedded in said closed end,
control means attached to the proximal ends of the outer catheter member and the inner catheter member, the proximal end of the deflection wire extending to the control means and the control means having an engaging means which fixedly engages said deflection wire, rotation of said engaging means causing the deflection wire to longitudinally displace either toward or away from the distal end of the inner catheter member, said displacement causing the distal end of the inner catheter member to bend away from or toward the line of the longitudinal axis of the inner catheter member, the control means having a passageway in fluid communication with the open lumen or lumens, and the engaging means of the control means fixedly engaging the deflection wire so that when the control means is rotated, the inner catheter member and the deflection wire both rotate together to cause the distal end of the inner catheter member to rotate about its longitudinal axis, and
a balloon dilatation catheter extending through an open lumen, the balloon dilatation catheter having distal and proximal ends, the distal end of the balloon dilatation catheter having inflatable dilatation balloon means adjacent to said distal end and protruding distally beyond the distal end of the inner catheter member, and the proximal end of the balloon dilatation catheter extending through the passageway in the control means.

31. The catheter means of claim 30 which also comprises a guide wire extending through an open lumen, the guide wire having distal and proximal ends, the distal end of the guide wire protruding distally beyond the distal end of the inner catheter member, and the proximal end of the guide wire extending through the passageway in the control means.

32. The catheter means of claim 30, wherein the balloon dilatation catheter has a guiding lumen therein, a guide wire having proximal and distal ends extends the length of the guiding lumen, the distal end of the balloon dilatation catheter protrudes distally beyond the distal end of the inner catheter member, and the proximal end of the guide wire extends proximally beyond the proximal end of the balloon dilatation catheter.

33. A steerable catheter means comprising:
an outer flexible catheter member having distal and proximal ends,
an inner flexible catheter member having distal and proximal ends and two or more lumens extending therethrough, one of said lumens being closed at its distal end, the other lumen or lumens being open at the distal end or ends thereof, the inner catheter member extending through the outer catheter member, and the distal end of the inner catheter member protruding distally beyond the distal end of the outer catheter member,
a deflection wire having distal and proximal ends and extending the length of the inner catheter member through the lumen having the closed end, the distal end of the deflection wire being embedded in said closed end,
control means attached to the proximal end of the outer catheter member and the inner catheter member, the proximal end of the deflection wire extending to the control means and the control means having an engaging means which fixedly engages said deflection wire, rotation of said engaging means causing the deflection wire to longitudinally displace either toward or away from the distal end of the inner catheter member, said displacement causing the distal end of the inner catheter member to bend away from or toward the line of the longitudinal axis of the inner catheter member, the control means having a passageway in fluid communication with the open lumen or lumens, and the engaging means of the control means fixedly engaging the deflection wire so that when the control means is rotated, the inner catheter member and the deflection wire both rotate together to cause the distal end of the inner catheter member to rotate about its longitudinal axis, and balloon dilatation means arranged on the outer surface of the distal ends of the outer catheter member and the inner catheter member.

34. The catheter means of claim 33 which also comprises a guide wire extending through an open lumen, the guide wire having distal and proximal ends, the distal end of the guide wire protruding distally beyond the distal end of the inner catheter member, and the proximal end of the guide wire extending through the passageway in the control means.

35. A steerable catheter means comprising:

an outer flexible catheter member having distal and proximal ends, an inner flexible catheter member having distal and proximal ends and two or more lumens extending therethrough, one of said lumens being closed at its distal end, the other lumen or lumens being open at the distal end or ends thereof, the inner catheter member extending through the outer catheter shell, the distal end of the inner catheter member protruding distally beyond the distal end of the outer catheter member, and the inner catheter member being movable within the outer catheter member, a deflection wire having distal and proximal ends and extending the length of the inner catheter member through the lumen having the closed end, the distal end of the deflection wire being embedded in said closed end, control means attached to the proximal end of the inner catheter member, the proximal end of the deflection wire extending through the control means and the control means having an engaging means which fixedly engages said deflection wire, rotation of said engaging means causing the deflection wire to longitudinally displace either toward or away from the distal end of the inner catheter member, said displacement causing the distal end of the inner catheter member to bend away from or toward the line of the longitudinal axis of the inner catheter member, the control means having a passageway in fluid communication with the open lumen or lumens, and the engaging means of the control means fixedly engaging the deflection wire so that when the control means is rotated, the inner catheter member and the deflection wire both rotate together to cause the distal end of the inner catheter member to rotate about its longitudinal axis, and a balloon dilatation catheter extending through an open lumen, the balloon dilatation catheter having distal and proximal ends, the distal end of the balloon dilatation catheter having inflatable dilatation balloon means adjacent to said distal end and protruding distally beyond the distal end of the inner catheter member, and the proximal end of the balloon dilatation catheter extending through the passageway in the control means.

36. The catheter means of claim 35, wherein the balloon dilatation catheter has a guiding lumen therein, a guide wire having proximal and distal ends extends the length of the guiding lumen, the distal end of the balloon dilatation catheter protrudes distally beyond the distal end of the inner catheter member, and the proximal end of the guide wire extends proximally beyond the proximal end of the balloon dilatation catheter.

37. The catheter means of claim 35 which also comprises a guide wire extending through an open lumen, the guide wire having distal and proximal ends, the distal end of the guide wire protruding distally beyond the distal end of the inner catheter member, and the proximal end of the guide wire extending through the passageway in the control means.

38. A steerable catheter means comprising:

an outer flexible catheter member having distal and proximal ends, an inner flexible catheter member having distal and proximal ends and two lumens extending therethrough, one of said lumens being closed at its distal end, the other lumen being open at its distal end, the inner catheter member extending through the outer catheter member, and the distal end of the inner catheter member protruding distally beyond the distal end of the outer catheter member, a deflection wire having distal and proximal ends and extending the length of the inner catheter member through the lumen having the closed end, the distal end of the deflection wire being embedded in said closed end, control means attached to the proximal ends of the outer catheter member and the inner catheter member, the proximal end of the deflection wire extending to the control means and the control means having an engaging means which fixedly engages said deflection wire, rotation of said engaging means causing the deflection wire to longitudinally displace either toward or away from the distal end of the inner catheter member, said displacement causing the distal end of the inner catheter member to bend away from or toward the line of the longitudinal axis of the inner catheter member, the control means having a passageway in fluid communication with the open lumen, and the engaging means of the control means fixedly engaging the deflection wire so that when the control means is rotated, the inner catheter member and the deflection wire both rotate substantially together to cause the distal end of the inner catheter member to rotate about its longitudinal axis, and a balloon dilatation catheter extending through the open lumen, the balloon dilatation catheter having distal and proximal ends, the distal end of the balloon dilatation catheter having inflatable dilatation balloon means adjacent to said distal end and protruding distally beyond the distal end of the inner catheter member, and the proximal end of the balloon dilatation catheter extending through the passageway in the control means.

39. The catheter means of claim 38, wherein the balloon dilatation catheter has a guiding lumen therein, a guide wire having proximal and distal ends extends the length of the guiding lumen, the distal end of the balloon dilatation catheter protrudes distally beyond the distal end of the inner catheter member, and the proximal end of the guide wire extends proximally beyond the proximal end of the balloon dilatation catheter.

40. A steerable catheter means comprising:

an outer flexible catheter member having distal and proximal ends, an inner flexible catheter member having distal and proximal ends and two lumens extending therethrough, one of said lumens being closed at its distal end, the other lumen being open at its distal end, the inner catheter member extending through the outer catheter member, and the distal end of the inner catheter member protruding distally beyond the distal end of the outer catheter member, a deflection wire having distal and proximal ends and extending the length of the inner catheter member through the lumen having the closed end, the distal end of the deflection wire being embedded in said closed end, control means attached to the proximal ends of the outer catheter member and the inner catheter member, the proximal end of the deflection wire extending to the control/means and the control means having an engaging means which fixedly engages said deflection wire, rotation of said engaging means causing the deflection wire to longitudinally displace either toward or away from the distal end of the inner catheter member, said displacement causing the distal end of the inner catheter member to bend away from or toward the line of the longitudinal axis of the inner catheter member, the control means having a passageway in fluid communication with the open lumen, and the engaging means of the control means fixedly engaging the deflection wire so that when the control means is rotated, the inner catheter member and the deflection wire both rotate substantially together to cause the distal end of the inner catheter member to rotate about its longitudinal axis, and balloon dilatation means arranged on the outer surfaces of the distal ends of the outer catheter member and the inner catheter member.

41. The catheter means of claim 40 which also comprises a guide wire extending through the open lumen, the guide wire having distal and proximal ends, the distal end of the guide wire protruding distally beyond the distal end of the inner catheter member, and the proximal end of the guide wire extending through the passageway in the control means.

42. A steerable catheter means comprising:

an outer flexible catheter member having distal and proximal ends, an inner flexible catheter member having distal and proximal ends and two lumens extending therethrough, one of said lumens being closed at its distal end, the other lumen being open at its distal end, the inner catheter member extending through the outer catheter member, the distal end of the inner catheter member protruding distally beyond the distal end of the outer catheter member, and the inner catheter being movable within the outer catheter member, a deflection wire having distal and proximal ends and extending the length of the inner catheter member through the lumen having the closed end, the distal end of the deflection wire being embedded in said closed end, control means attached to the proximal end of the inner catheter member, the proximal end of the deflection wire extending to the control means and the control means having an engaging means which fixedly engages said deflection wire, rotation of said engaging means causing the deflection wire to longitudinally displace either toward or away from the distal end of the inner catheter member, said displacement causing the distal end of the inner catheter member to bend away from or toward the line of the longitudinal axis of the inner catheter member, the control means having a passageway in fluid communication with the open lumen, and the engaging means of the control means fixedly engaging the deflection wire so that when the control means is rotated, the inner catheter member and the steering wire both rotate substantially together to cause the distal end of the inner catheter member to rotate about its longitudinal axis, and a balloon dilatation catheter extending through the open lumen, the balloon dilatation catheter having distal and proximal ends, the distal end of the balloon dilatation catheter having inflatable dilatation balloon means adjacent to said distal end and protruding distally beyond the distal end of the inner catheter member, and the proximal end of the balloon dilatation catheter extending through the passageway in the control means.

43. The catheter means of claim 42, wherein the balloon dilatation catheter has a guiding lumen therein, a guide wire having proximal and distal ends extends the length of the guiding lumen, the distal end of the balloon dilatation catheter protrudes distally beyond the distal end of the inner catheter member, and the proximal end of the guide wire extends proximally beyond the proximal end of the balloon dilatation catheter.

* * * * *

UNITED STATES PATENT AND TRADEMARK OFFICE
CERTIFICATE OF CORRECTION

PATENT NO. : 4,960,411

DATED : October 2, 1990

INVENTOR(S) : Maurice Buchbinder

It is certified that error appears in the above-identified patent and that said Letters Patent is hereby corrected as shown below:

On the cover page, first column, at line number [54] and in column 1, lines 2 and 3, the title "LOW PROFILE STERRABLE SOFT-TIP CATHETER" should read -- LOW PROFILE STEERABLE SOFT-TIP CATHETER --.

Signed and Sealed this

First Day of October, 1991

Attest:

*Attesting Officer*

HARRY F. MANBECK, JR.

*Commissioner of Patents and Trademarks*